United States Patent [19]

Klausz

[11] Patent Number: 4,670,896
[45] Date of Patent: Jun. 2, 1987

[54] RADIOLOGY INSTALLATION WITH COMPENSATING FILTER(S)

[75] Inventor: Remy Klausz, Neully sur Seine, France

[73] Assignee: Thomson-CGR, Paris, France

[21] Appl. No.: 712,368

[22] Filed: Mar. 18, 1985

[30] Foreign Application Priority Data

Mar. 20, 1984 [FR] France .................. 84 04287

[51] Int. Cl.⁴ ............................. G21K 3/00
[52] U.S. Cl. ..................... 378/156; 378/159; 378/206
[58] Field of Search ............... 378/156–159, 378/206

[56] References Cited

U.S. PATENT DOCUMENTS 3,717,768  2/1973  Edholm et al. .................. 378/206

FOREIGN PATENT DOCUMENTS 0062400  5/1980  Japan .......................... 378/156
2017450  10/1979  United Kingdom .

OTHER PUBLICATIONS

IEEE Transactions on Bio-Medical Engineering, vol. BME-21, No. 3, May 1974, pp. 243–244, New York, U.S., E. E. Hoefer et al., "Computer-Controlled Synthesis of Tomograms by Means of a TV Storage Tube".

Primary Examiner—Craig E. Church
Assistant Examiner—John C. Freeman
Attorney, Agent, or Firm—Oblon, Fisher, Spivak, McClelland & Maier

[57] ABSTRACT

Installation allowing the adjustment of compensating filters without exposure to permanent irradiation. According to one possible embodiment, a radiological image is taken (source, brightness or luminance amplifier) and memorized in an image memory prior to being projected by the video projector onto the patient by through-crossing the filter, this filter having brightness absorption and X-ray absorption properties which are similar.

13 Claims, 2 Drawing Figures

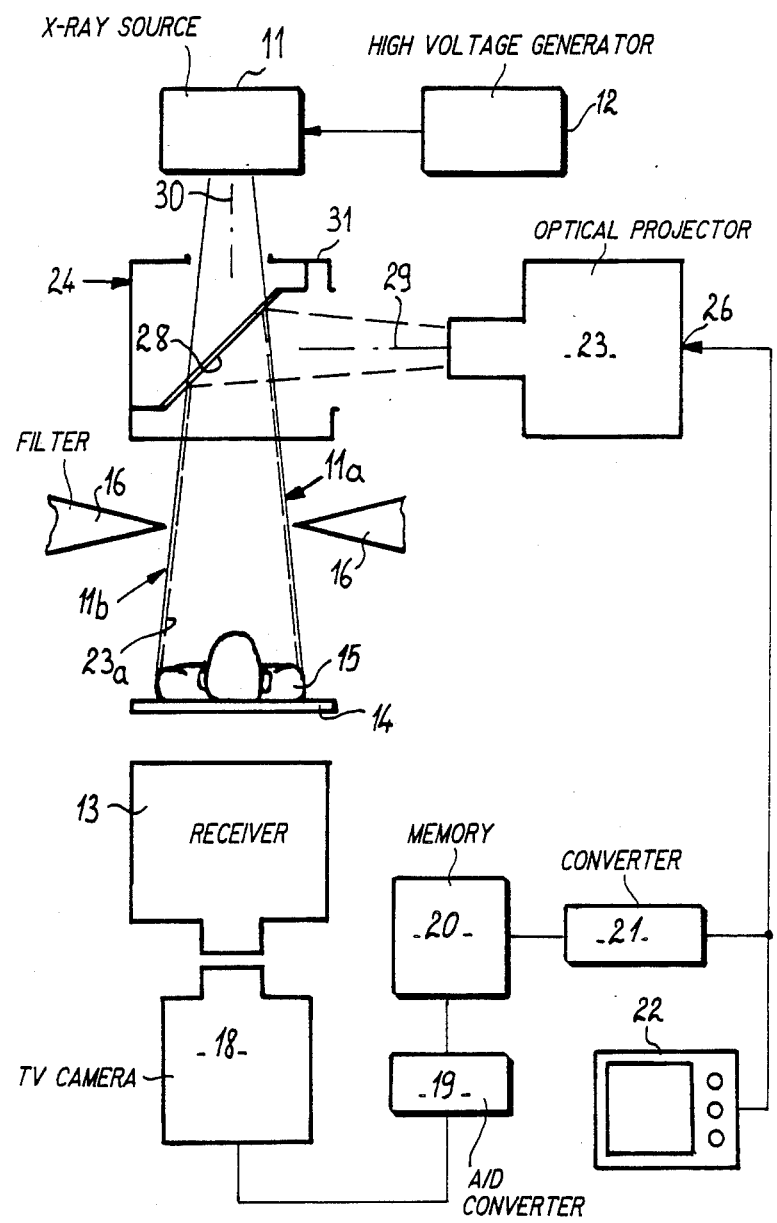

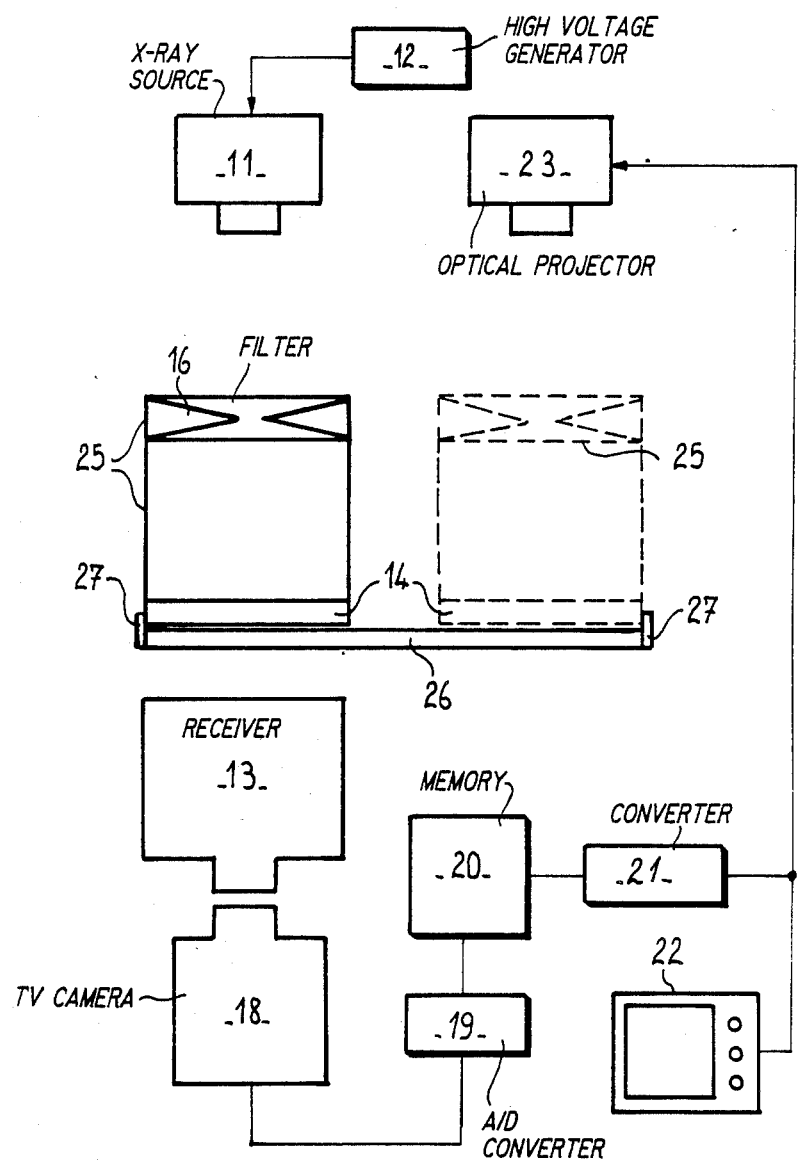
FIG_2

RADIOLOGY INSTALLATION WITH COMPENSATING FILTER(S)

BACKGROUND OF THE INVENTION

1. Field of the Invention

The present invention concerns a radiology installation with compensating filter(s) and relates, more particularly, to novel positioning means for such a filter.

2. Summary of the Prior Art

It is known that in a radiology installation, the differences of thickness and density of the portion of the patient who is in the X-ray field are sometimes such that the "modulation" of the beam by the subject exceeds the dynamics of the detector. It is known to interpose structures having determined shapes and thickness in function, especially, of the nature (average density) of the tissues above which they must be placed. These compensating structures or filters comprising elements whose positions are adjustable have, for many years, been made of aluminum. More recently, filters made of transparent plastic material loaded with lead have been proposed, which solution allows, in particular, to maintain the luminous positioning beam (symbolizing the X-ray beam) during positioning and adjustment of the filters. Nevertheless, the efficiency of these adjustments depends largely on the skill of the operator at least for carrying them out in radioscopic mode, which presents other drawbacks. Indeed, on the one hand, the patient is subjected to a further exposure to irradiation, which is not directly useful to the diagnosis, while, on the other hand, during the length of service the operator often has his hands and forearms directly exposed to the X-ray beam.

The present invention aims at least to allow a more accurate and more rapid positioning of the compensating filter(s). It also aims at reducing as much as possible the irradiation doses received by both the patient and the operator.

With this purpose, the invention principally concerns a radiology installation, comprising an X-ray source, a receiver and at least one adjustable compensating filter, normally placed within the volume in which is inscribed the X-ray beam, wherein it comprises optical means for projecting a radiological image established by the said receiver and means for placing the said filter, at least during an adjustment phase, within the volume in which is inscribed the said beam of the said image and wherein the said compensating filter has partial absorption properties both in the field of X-rays and in the field of visible light.

According to one possible embodiment, the installation comprises means for deflecting the beam of the image, these means being disposed so that a portion of the volume in which the said beam of the said image is inscribed substantially coincides with a portion of the volume in which the said X-ray beam is inscribed, the filter being situated within this common portion of the volume.

In the majority of modern radiology installations, an image memory is interconnected between the detector (generally a luminance or brightness amplifier) and visualization means. In order to solve completely the frequent irradiation problem of the operator, it is possible to use this memory within the framework of the present invention.

More precisely, the invention also concerns an installation of the type mentioned herein-above comprising an image memory connected to the said receiver so as to memorize a series of digital data that is representative of a radiological image, the said memory being of the cyclical and autonomous reading type, wherein a video projector having its signal input connected to the output of the said memory is disposed so that its axis of optical projection is substantially perpendicular to the axis of the X-ray beam and wherein a mirror is interposed in the volume within which the said X-ray beam is inscribed at 45° with respect to the said optical proection axis.

Therefore, a pulsated emission of the X-ray source, having a relatively short duration, is sufficient to register in the memory the representative data of a radiological image, which is then projected onto the patient's body (or on to a screen placed upon him) which allows to adjust the position of the compensating filter without requiring the presence of an X-ray beam.

In the case where, for example, a monochromatic radiological image is projected upon the patient, a correct adjustment of the filter is obtained when the projected image has relatively slight contrasts.

BRIEF DESCRIPTION OF THE DRAWINGS

The invention and its advantages objects and features will become more apparent through reading the following description of a currently preferred embodiment of an installation according to its principle, given by way of non-limitative example and made with reference to the appended drawings in which:

FIG. 1 represents schematically a radiological installation incorporating the improvements according to the present invention; and FIG. 2 represents schematically a variant of the installation.

DETAILED DESCRIPTION OF A PREFERRED EMBODIMENT

FIG. 1 represents a radiology installation comprising an X-ray source 11 fed by a high voltage generator 12 and emitting an X-ray beam 11a in the direction of a receiver 13 constituted in the present embodiment by a luminance amplifier. A patient-screening table 14 is placed within the X-ray beam 11a, between the source and the receiver. The subject to be examined 15 is positioned on the table, and, inorder to take into account the difference of thickness and average density of the examined areas situated in the field of beam 11a, a compensating filter 16 having adjustable positioning is disposed in beam 11a, between the source and the subject. The form and the thickness (which are both variable) of this filter depend upon the area of the body to be examined. An installation of the type described thus comprises as accessories, a set of such filters with the movable portions having different forms and dimensions in function of the principal types of radiological examinations.

The installation comprises, furthermore, a television camera 18 associated to receiver 13 in order to pick up the radiological image formed in said receiver, an analog-digital converter 19 receiving the signals issuing from the camera, an image memory 20 connected to the output of converter 19, a digital-analog converter 21 connected to the output of the memory and a television receiver 22 connected to the output of the converter 21 and on which is displayed normally the radiological image. All the sub-assemblies cited herein-above are classic and exist within the majority of modern radiology installations. In particular, image memory 20 has enough capacity to stock in digital form all the data necessary for the reproduction of an image reconstituted by receiver 13. It has an autonomous cyclical reading operating mode, operating at a rhythm sufficiently rapid to maintain a visible image on the screen of the television receiver 22.

In order to operate the invention, filters 16 must have partial adsorption properties in both the X-ray field and in the visible light field. To do this could be possible to utilize filters made of plastic material loaded with lead, partially absorbing light, similar to those that are manufactured, a coloring material (pigment) (or dye) which ensures attenuation in the field of visible light. The lead loads and colouring material will be controlled so that at all points of the filter, the brightness attenuation is substantially proportional to the attenuation of the X-rays.

The installation comprises, furthermore, optical projection means 23 of the radiological image established by receiver 13 and means 24 for deflecting the beam of the said image. The deflecting means 24 are disposed so that one portion 23a of the volume within which is inscribed the image beam substantially coincides with a portion 11b of the volume within which is inscribed the X-ray beam, compensating filter 16 being situated in this common portion of the volume.

According to the example, optical projection means 23 comprise essentially a video projector the signal input 26 of which is connected to the output of converter 21, i.e. downstream from memory 20 in the restitution chain of the radiological image described hereinabove, while deflecting means 24 essentially comprise a mirror 28 interposed in the volume within which is inscribed the X-ray beam. More specifically, projector 23 is disposed so that its axis of optical projection 29 is perpendicular to the axis 30 of the X-ray beam and the mirror 28 is mounted in a housing 31 in order to create an angle of 45° with respect to the axis of optical projection 29. Housing 31 is interposed between the output of the source 11 and the site of the filters 16. If the mirror is fixed within the housing 29, it will be constituted of a substantially radio-transparent material. This type of mirror is classic, it already exists in collimators to reflect the beam issuing from an incandescent lamp. However, due to the fact the installation comprises an image memory 20, it is also possible to utilize a movable mirror (for example, pivoting about a lateral axis) allowing its disengagement from the volume in which is inscribed the X-ray beam, during the time necessary for the formation of the image and its memorization. Operating the installation described herein-above for adjusting the compensating filters is carried out as follows.

The patient being in position on the table 14, a pulsated emission is ordered from the X-ray source 11, of brief duration sufficient to acquire the radiological image and memorize it in memory 20. During this brief radiation of the patient, the operator may remain at a distance. Then, the data read cyclically in memory 20 are applied to the input of the video projector 23 and the radiological image is projected onto the body itself of the patient after being reflected on mirror 28. The operator thus disposes of all the time he may need to manoeuvre into position the movable parts of the compensating filter 16 so as to attenuate the greatest contrasts projected onto the patient. The radiological examination per se can thus begin, by exploiting to a maximum the dynamic of luminance amplifier 13.

It is possible to utilize other means to project the radiological image onto the patient. For example, the video projector can be replaced by an arrangement comprising a laser beam generator, means for scanning this beam and means for modulating the beam connected to image memory 20. It is also possible to replace the video projector by a simple incandescent lamp having a relatively punctual focus and to interpose between mirror 28 and compensating filter 16 a plane blade defining a matrix of modulated in transmission cells, for example, with liquid crystals, the different cells being linked to the image memory.

It is also possible to envisage an installation in which the X-ray beam and the image beam do not comprise a common portion to the filter. The filter is therefore mounted on a movable support between two predetermined positions, one adjustment position, where it is located in the image beam and a utilization position where it is located in the X-ray beam. FIG. 2 illustrates this arrangement. According to this embodiment, where the structure elements analogue to those of FIG. 1 bear the same numerical references, filter 16 is mounted in a supporting frame 25 integral with the patient-screening table 14 and this latter is subject to being displaced, laterally along the length of rails 26 between the two predetermined positions by a system of abutments 27 or analogue. The first position represented in continuous lines in FIG. 2 is the normal radiological examination position, the second position represented in a dashed line is such that the video protector 23 can replace the X-ray source; this is the adjustment position of the filter. The utilization manner of this installation is thus one of the most simple. The patient lines on table 14 underneath the supporting frame of filter 16 and the table is placed underneath the X-ray source 11. A radiological image is revealed in these conditions by the brief operation of the source 11. Table 14 is thereafter displaced laterally in order to arrive in adjustment position underneath video projector 23. The radiological image is thus projected during the whole time necessary for the adjustment of the filter. Table 14 is thereafter brought back to examination position underneath X-ray source 11.

I claim:

1. A radiological installation, comprising: an x-ray source for projecting a short pulsed x-ray beam; a support for an object placed within said beam; at least one adjustable compensating filter, normally placed within said x-ray beam, between said source and said support; said compensating filter partially absorbing both x-rays and visible light; means for receiving x-rays that have passed through said filter and said object and for converting the resulting x-ray image into an electrical television signal; means for storing said television signal; means for displaying said television signal as a visible image; and means for projecting a beam of said visible image through said filter and onto said object so that the visible image of the object precisely overlaps the object.

2. A radiological installation according to claim 1, wherein at any point of said filter, the visible image attenuation is substantially proportional to the attenuation of the X-rays.

3. A radiological installation according to claim 1, further comprising: a means for deflecting the beam of the visible image disposed such that a portion of the volume in which said deflected beam of said visible image is inscribed substantially coincides with a portion of the volume in which the said X-ray beam is inscribed, the filter being situated within this common portion of the volume.

4. A radiological installation according to claim 1, wherein said filter is mounted on a support which is movable between two predetermined positions, wherein the two positions are respectively an adjustment position where the said filter is situated in the eam of the said image and a utilization position where the said filter is situated in the X-ray beam.

5. A radiological installation according to claim 4, wherein said support is integral with a movable patient table, on which said object is placed, and wherein the two predetermined position are defined by a given displacement of the said table.

6. A radiological installation according to claim 4, further comprising: means to output a series of digital data from said receiver; an image memory connected to said receiver; to memorize the series of digital data outputted by said receiver which is representative of a radiological image, wherein said memory is cyclical and of the autonomous reading type and wherein said memory is connected to said visible projection means.

7. A radiological installation according to claim 3, further comprising:
   means to output a series of digital data, which is representative of a radiological image,
   an image memory connected to said receiver so as to memorize the series of digital data outputted by said receiver that is representative of a radiological image wherein said memory is of the cyclical and autonomous reading type, and further wherein a video projector having its signal input connected to the output of the said memory is disposed such that the axis of optical projection of said projector is substantially perpendicular to the axis of the X-ray beam; and a mirror interposed, in the volume within which said X-ray beam is inscribed, at 45° with respect to said optical projection axis.

8. A radiological installation according to claim 7, wherein said mirror is fixed in position and is essentially radiotransparent.

9. A radiological installation according to claim 7, wherein said mirror is movably mounted so as to be removable from the volume within which said X-ray beam is inscribed.

10. A radiological installation according to claim 1, wherein said compensating filter is made of a partially visible light absorbing plastic material.

11. A radiological installation according to claim 10, wherein said compensating filter is made of colored plastic material containing lead.

12. A radiological installation according to claim 2, further comprising for deflecting the beam of the image, these means being disposed so that a portion of the volume in which said beam of said image is inscribed, substantially coincides with a portion of the volume in which the said X-ray beam is inscribed, the filter being situated within this common portion of the volume.

13. A radiological installation according to claim 2, wherein said filter is mounted on a support which is movable between two predetermined positions, wherein the two positions are respectively an adjustment position where said filter is situated in the beam of the said visible image and a utilization position where said filter is situated in the X-ray beam.

* * * * *